United States Patent
Crocker et al.

(10) Patent No.: US 6,939,964 B2
(45) Date of Patent: *Sep. 6, 2005

(54) CRYSTAL FORMS OF (-)-6-CHLORO-4-CYCLOPROPYLETHYNYL-4-TRIFLUOROMETHYL-1,4-DIHYDRO-2H-3,1-BENZOXAZIN-2-ONE

(75) Inventors: Louis S. Crocker, Belle Mead, NJ (US); Joseph L. Kukura, II, Somerset, NJ (US); Andrew S. Thompson, Mountainside, NJ (US); Christine Stelmach, Westfield, NJ (US); Steven D. Young, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/891,749

(22) Filed: Jun. 24, 2004

(65) Prior Publication Data
US 2004/0259872 A1 Dec. 23, 2004

Related U.S. Application Data

(60) Continuation of application No. 10/447,690, filed on May 29, 2003, now abandoned, which is a continuation of application No. 10/000,537, filed on Oct. 19, 2001, now Pat. No. 6,639,071, which is a continuation of application No. 09/282,744, filed on Mar. 31, 1999, now abandoned, which is a division of application No. 09/008,824, filed on Jan. 20, 1998, now Pat. No. 5,965,729.
(60) Provisional application No. 60/037,385, filed on Feb. 5, 1997, and provisional application No. 60/042,807, filed on Apr. 8, 1997.

(51) Int. Cl.$^7$ ............................................. C07D 265/18
(52) U.S. Cl. ....................................................... 544/92
(58) Field of Search ........................................... 544/92

(56) References Cited

U.S. PATENT DOCUMENTS

| | | | |
|---|---|---|---|
| 4,518,597 A | 5/1985 | Narr et al. | |
| 5,519,021 A | 5/1996 | Young et al. | |
| 5,633,405 A | 5/1997 | Thompson et al. | |
| 5,633,467 A | 5/1997 | Thompson et al. | |
| 6,639,071 B2 | 10/2003 | Crocker et al. | |
| 6,673,372 B1 * | 1/2004 | Radesca et al. | 424/489 |

FOREIGN PATENT DOCUMENTS

| | | |
|---|---|---|
| EP | 0 169 618 | 1/1986 |
| EP | 0 582 455 | 2/1994 |
| WO | WO 95/20389 | 8/1995 |
| WO | WO 96/37457 | 11/1996 |
| WO | WO 98/04535 | 2/1998 |
| WO | WO 98/14436 | 4/1998 |
| WO | WO 98/45278 | 10/1998 |
| WO | WO 99/64405 | 12/1999 |

OTHER PUBLICATIONS

T. L. Threifall, "Analysis of Organic Polymorphs," Analyst, vol. 120, pp. 2435–2460 (Oct. 1995).

D. Giron, "Thermal Analysis and Calorimetric Methods in the Characterization of Polymorphs and Solvates," Thermochimica Acta, vol. 248, pp. 1–59 (1995).

A. S. Thompson et al., "Use of an Ephedrine Alkoxide to Mediate Enantioselective Addition of an Acetylide to a Prochiral Ketone: Assymmetric Synthesis of the Reverse Transcriptase Inhibitor L–743,726," Tetrahedron Letters, vol. 36, No. 49, pp. 8937–8940 (1995).

* cited by examiner

Primary Examiner—Richard L. Raymond
(74) Attorney, Agent, or Firm—Kenneth R. Walton; Valerie J. Camara

(57) ABSTRACT

The instant invention describes a method for crystallizing (–)-6-chloro-4-cyclopropylethynyl-4-trifluoromethyl-1,4-dihydro-2H-3,1-benzoxazin-2-one from a solvent and antisolvent solvent system and producing the crystalline product. The desired final crystal form, Form I, can be produced when using methanol or ethanol. Form II is isolated from 2-propanol and can be converted to the desired crystal form at low drying temperatures, such as between about a temperature of 40° C. and 50° C.

14 Claims, 7 Drawing Sheets

Figure 1 Controlled Anti-solvent Addition

Figure 2 Heel Crystallization

CRYSTAL FORMS OF (-)-6-CHLORO-4-CYCLOPROPYLETHYNYL-4-TRIFLUOROMETHYL-1,4-DIHYDRO-2H-3,1-BENZOXAZIN-2-ONE

This application is a continuation of U.S. application Ser. No. 10/447,690, filed May 29, 2003, abandoned; which is a continuation of U.S. application Ser. No. 10/000,537, filed Oct. 19, 2001, now U.S. Pat. No. 6,639,071; which is a continuation of U.S. application Ser. No. 09/282,744, filed Mar. 31, 1999, abandoned; which is a divisional of U.S. application Ser. No. 09/008,824, filed Jan. 20, 1998, now U.S. Pat. No. 5,965,729; which claims the benefit of U.S. provisional application Ser. Nos. 60/037,385, filed Feb. 5, 1997 and 60/042,807, filed Apr. 8, 1997.

BACKGROUND OF THE INVENTION

The synthesis of the reverse transcriptase inhibitor (RTI), (-)-6-chloro-4-cyclopropylethynyl-4-trifluoromethyl-1,4-dihydro-2H-3,1-benzoxazin-2-one, also known as DMP-266 has been described in U.S. Pat. No. 5,519,021 issued on May 21, 1996 and the corresponding PCT International Patent Application WO 95/20389, which published on Aug. 3, 1995. Additionally, the asymmetric synthesis of an enantiomeric benzoxazinone by a highly enantioselective acetylide addition and cyclization sequence has been described by Thompson, et al., Tetrahedron Letters 1995, 36, 937–940, as well as the PCT publication, WO 96/37457, which published on Nov. 28, 1996.

The compound was previously crystallized from a heptane-tetrahydrofuran (THF) solvent system. The crystallization procedure required the use of high temperatures (about 90° C.) to dissolve the final product. Crystals formed by nucleation during the cooling process. The crystals which were produced were Form II and are converted to the desired Form I while drying under vacuum at 90° C. This crystallization provided minimal purification and produced material with inconsistent physical properties. The final product slurry was extremely difficult to mix and handle due to its high viscosity and heterogeneous nature.

The instant invention describes a method for crystallizing (-)-6-chloro-4-cyclopropylethynyl-4-trifluoromethyl-1,4-dihydro-2H-3,1-benzoxazin-2-one from a solvent and anti-solvent solvent system and producing the crystalline product. The desired final crystal form, Form I, can be produced when using methanol or ethanol. Form II is isolated from 2-propanol and can be converted to the desired crystal form at low drying temperatures, as low at 40° C.

SUMMARY OF THE INVENTION

A process for the crystallization of a compound of the structural formula

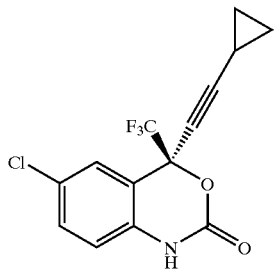

comprising the use of a solvent to effect the dissolution of the compound followed by the addition of an anti-solvent to initiate the crystallization.

DETAILED DESCRIPTION OF THE INVENTION

Figure 1:
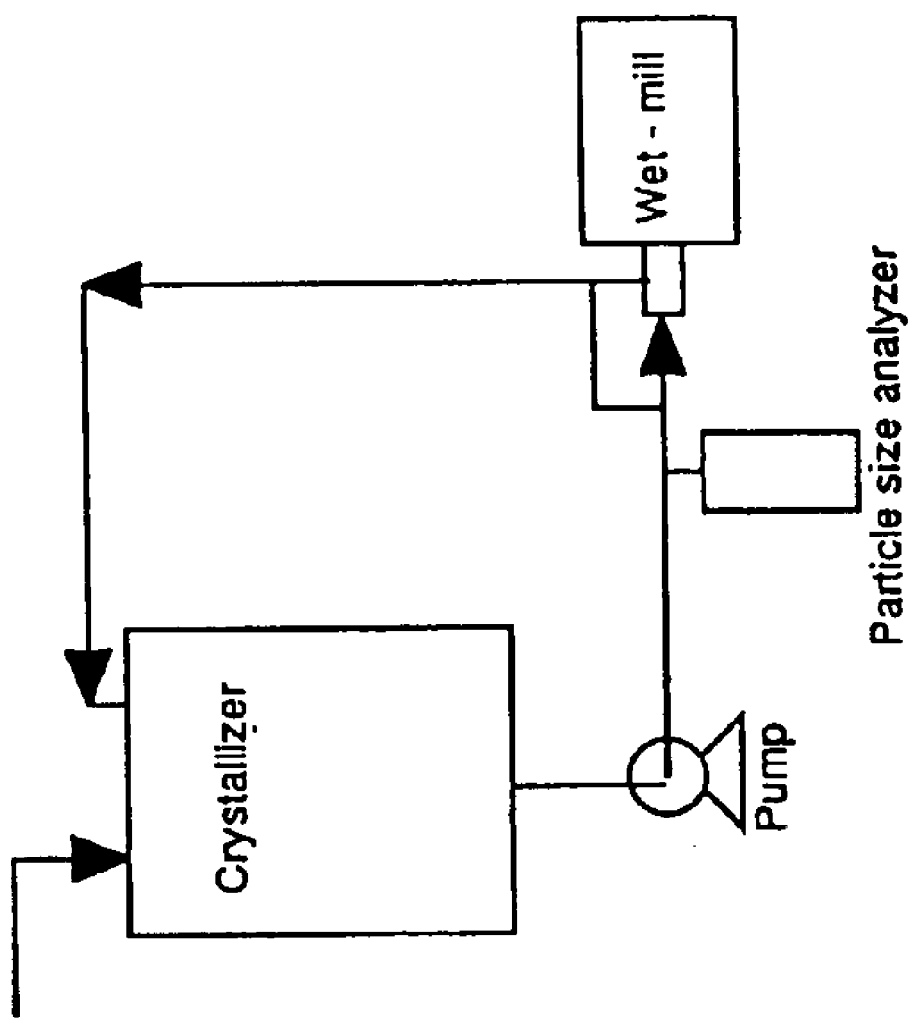
FIG. 1. Flowsheet of the controlled anti-solvent addition crystallization method.

A process for the crystallization of a compound of the structural formula

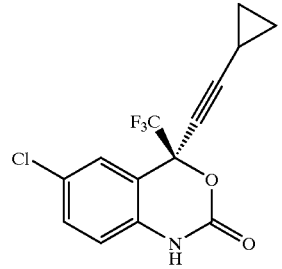

comprising the use of a solvent to effect the dissolution of the compound followed by the addition of an anti-solvent to initiate crystallization.

A process for the crystallization of a compound of the structural formula

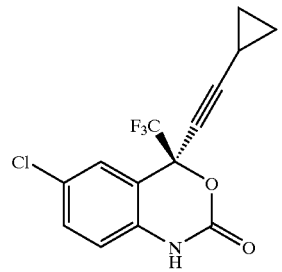

comprising the steps of:
 (1) dissolving the compound in a solvent in a ratio of about 3.0 ml to about 10.0 ml of solvent to 1 gram of the compound;
 (2) filtering the solution of the compound to remove any particulate matter;
 (3) adding the anti-solvent to the stirring solution at room temperature over a period of about 30 minutes to about an hour to reach the saturation point of the solution containing the compound;

(4) adding to the solution a solid seed charge of the compound in the amount of about 2 to about 10 percent by weight to form a slurry;
(5) milling the slurry to reduce the thickness of the slurry;
(6) adding the remaining water to reach the desired solvent composition of about 30% to about 50% and milling the slurry as needed during the addition;
(7) slowly cooling the slurry to about 5° C. to about 20° C.;
(8) aging for about 2 to about 16 hours until the supernatant concentration reaches equilibrium;
(9) milling the slurry, as needed, to reduce the thickness of the slurry;
(10) filtering the milled slurry to isolate a wet cake of the crystalline compound;
(11) washing the wetcake once with about 1 to about 2 bed volumes of the final crystallization solvent composition and then twice with water using about 5–10 ml water per gram of compound; and
(12) drying the washed wetcake at about 40° C. to about 90° C. under vacuum for about 1 hour to about 3 days, or until the loss on dryness is less than 0.5 weight percent.

The controlled anti-solvent crystallization process as recited above wherein the solvent is defined as alcohol, wherein alcohol is a straight or branched chain $(C_1-C_6)$-alkanol. A preferred embodiment of the solvents useful in the controlled anti-solvent crystallization process is $(C_1-C_6)$-alkanol, such as, methanol, ethanol, and 2-propanol. The preferred alcohol is 2-propanol.

The preferred alcohol is 2-propanol for reasons relating to obtaining consistent crystal forms. Although methanol and ethanol solvent systems have been shown to be capable of producing the desired Form I crystal structure, a slight contamination of Form III crystals in a crystallization slurry in these systems can convert the entire slurry to containing exclusively Form III crystals, which are relatively difficult to convert to the desired Form I structure. Any known crystal structure of this compound placed in an about 25% to 35% (v/v) 2-propanol-water solvent system has been shown to quickly convert to the Form II crystal structure, which can readily convert to the desired Form I crystal structure during drying.

The anti-solvent as recited above is defined as a solvent in which the compound has limited solubility. In the instant process, the preferred anti-solvent is water.

The temperature of the solution during the anti-solvent addition (Step 3) was about 20° C. to about 25° C. The temperature of the slurry being about 5° C. to about 20° C., and preferrably at about 10° C.

The temperature used during the drying of the washed wetcake (Step 12) is about 40° C. to about 90° C., and preferrably about 40° C. to about 60° C.

The solvent system (solvent plus anti-solvent) used ranged from about 30% to about 50% solvent volume to anti-solvent volume (v/v) ratio. The total volume of the solvent system ranging from about 12 to about 20 ml of the solvent system per gram of the compound. The solvent volume to anti-solvent volume ratio for selected solvent systems is as follows: 1) an ethanol-water solvent system is about 30% to about 40% ethanol to water v/v ratio; 2) a methanol-water solvent system is about 40% to about 50% methanol to water v/v ratio; and 3) an 2-propanol-water solvent system is about 25% to about 35% 2-propanol to water v/v ratio. The perferred solvent system is 2-propanol-water used in about a 30% volume to volume ratio and a total solvent system volume of about 15 ml per gram of the compound.

A process for the crystallization of a compound of the structural formula

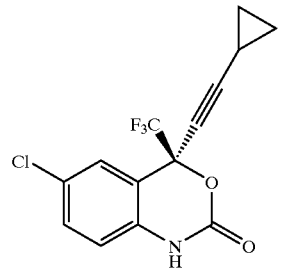

comprising the steps of:
(1) mixing about 10% to about 20% by weight of the final amount of (−)-6-chloro-4-cyclopropylethynyl-4-trifluoromethyl-1,4-dihydro-2H-3,1-benzoxazin-2-one in the desired v/v ratio of solvent to anti-solvent at about 20° C. to form the heel or retaining a final slurry from a previous batch;
(2) adding the solution of solvent and (−)-6-chloro-4-cyclopropylethynyl-4-trifluoromethyl-1,4-dihydro-2H-3,1-benzoxazin-2-one, and anti-solvent to the heel simultaneuosly at constant rates over about 6 hours maintaining the v/v ratio of solvent to anti-solvent;
(3) milling the slurry during the addition to reduce the thickness of the slurry;
(4) cooling the slurry to about 10° C. over about 3 hours and aging slurry until the supernatant concentration reaches equilibrium;
(5) filtering the milled slurry to isolate a wet cake of the crystalline compound;
(6) washing the wetcake once with about 1 to about 2 bed volumes of the final crystallization solvent composition and then twice with water using about 5 ml to about 10 ml water per gram of compound; and
(7) drying the washed wetcake at about 40° C. to about 90° C. under vacuum for about 1 hour to about 3 days, or until the loss on dryness is less then 0.5 weight percent.

The heel crystallization process as recited above wherein the solvent is defined as acetonitrile, dimethyl acetamide, dimethyl formamide or alcohol. A preferred embodiment of the solvents useful in the controlled anti-solvent crystallization process is alcohol, wherein alcohol is defined as $(C_1-C_6)$-alkanol, such as, methanol, ethanol, and 2-propanol. The preferred alcohol is 2-propanol.

The anti-solvent as recited above is defined as a solvent in which the compound has limited solubility. In the heel crystallization process the preferred anti-solvent is water.

The process as recited above wherein the temperature of the solution during the anti-solvent addition is about 5° C. to about 20° C.

The temperature used during the drying of the washed wetcake is about 40° C. to about 90° C., and preferrably about 40° C. to about 60° C.

The solvent system (solvent plus anti-solvent) used ranges from about 30% to about 50% solvent volume to anti-solvent volume (v/v) ratio. The total volume of the solvent system ranging from about 12 to about 20 ml of the solvent system per gram of the compound. The solvent to anti-solvent volume to volume ratio for selected solvent systems is as follows: 1) an ethanol-water solvent system is about 30% to about 40% ethanol to water v/v ratio; 2) a methanol-water solvent system is about 40% to about 50% methanol to water v/v ratio; and 3) an 2-propanol-water solvent system is about 25% to about 35% 2-propanol to water v/v ratio. The perferred solvent system is 2-propanol-water used in about a 30% volume to volume ratio and a total solvent system volume of about 15 ml per gram of the compound.

Figure 3:
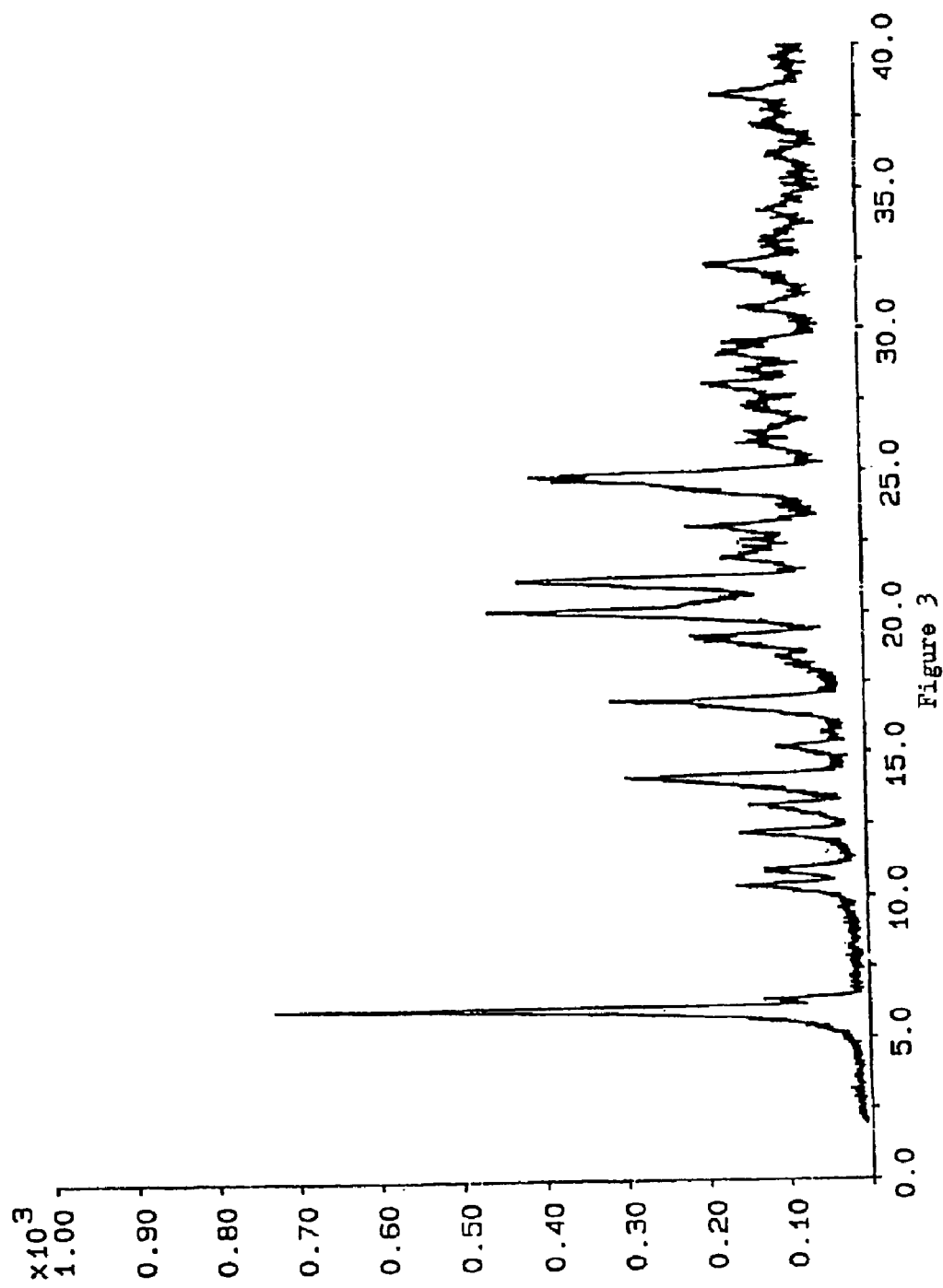
FIG. 3. X-ray powder diffraction pattern for Form I of (-)-6-chloro-4-cyclopropylethynyl-4-trifluoromethyl-1,4-dihydro-2H-3,1-benzoxazin-2-one.
Figure 4:
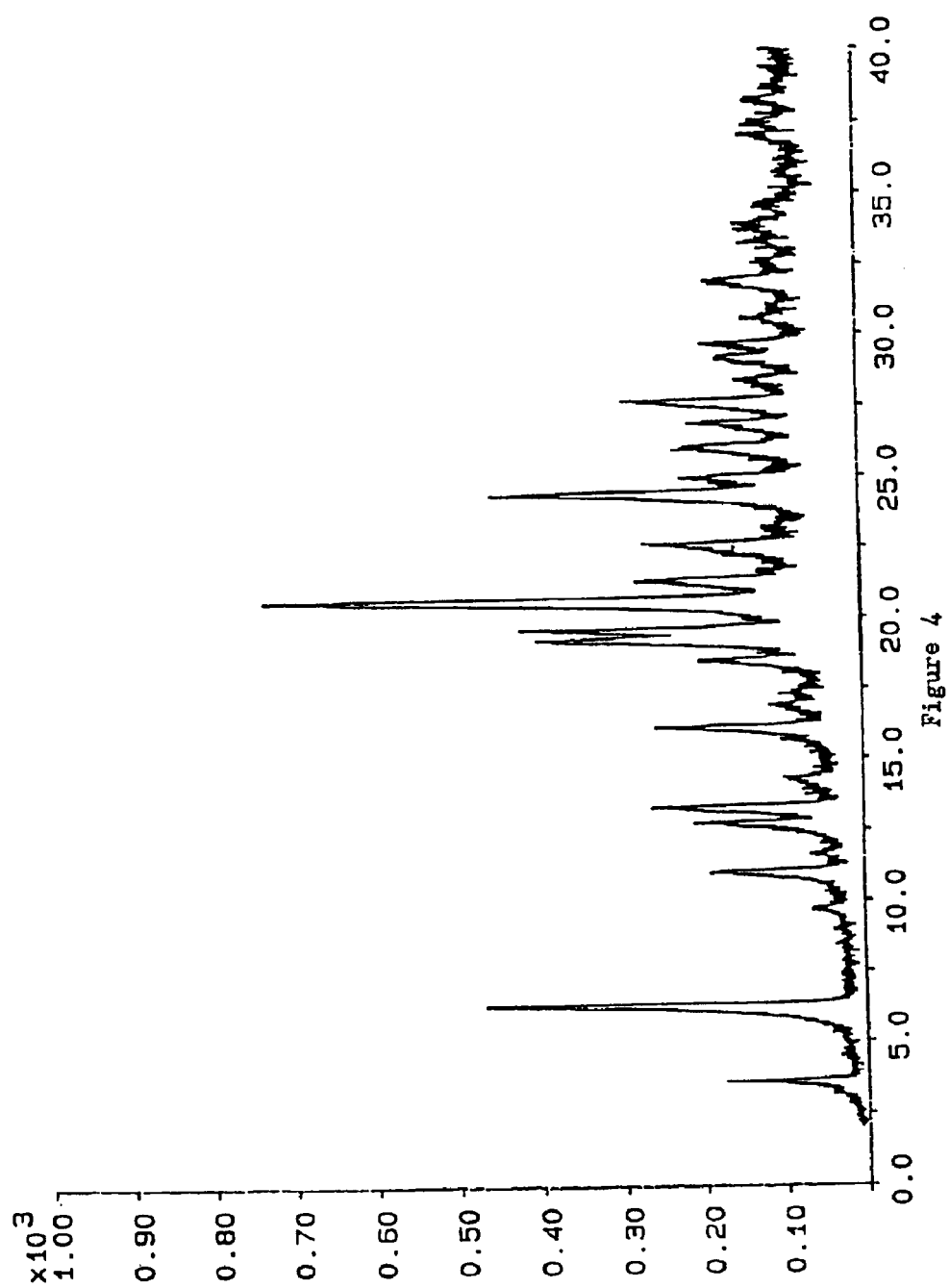
FIG. 4. X-ray powder diffraction pattern for Form II of (-)-6-chloro-4-cyclopropylethynyl-4-trifluoromethyl-1,4-dihydro-2H-3,1-benzoxazin-2-one.
Figure 5:
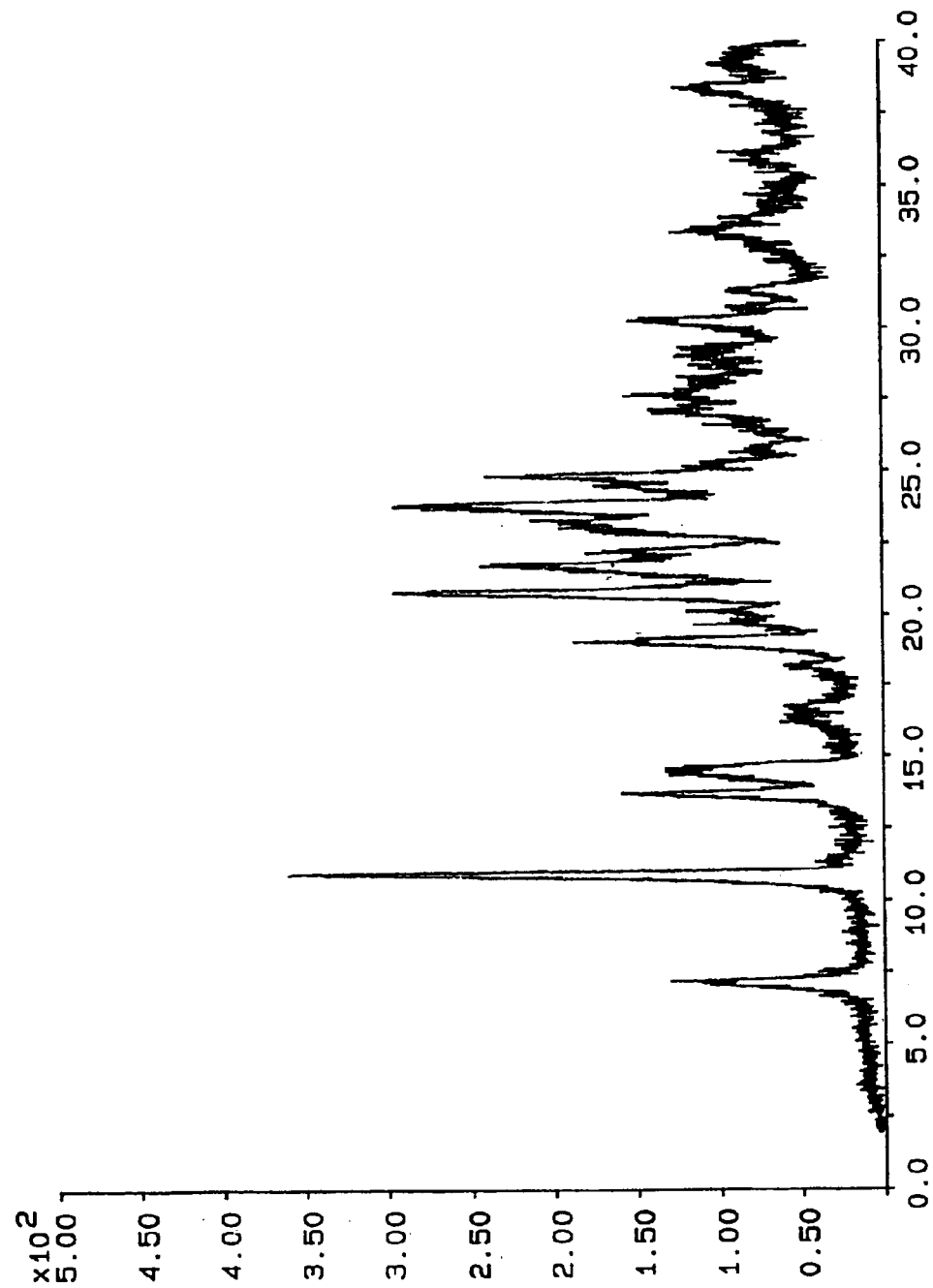
FIG. 5. X-ray powder diffraction pattern for Form III of (-)-6-chloro-4-cyclopropylethynyl-4-trifluoromethyl-1,4-dihydro-2H-3,1-benzoxazin-2-one.
Figure 6:
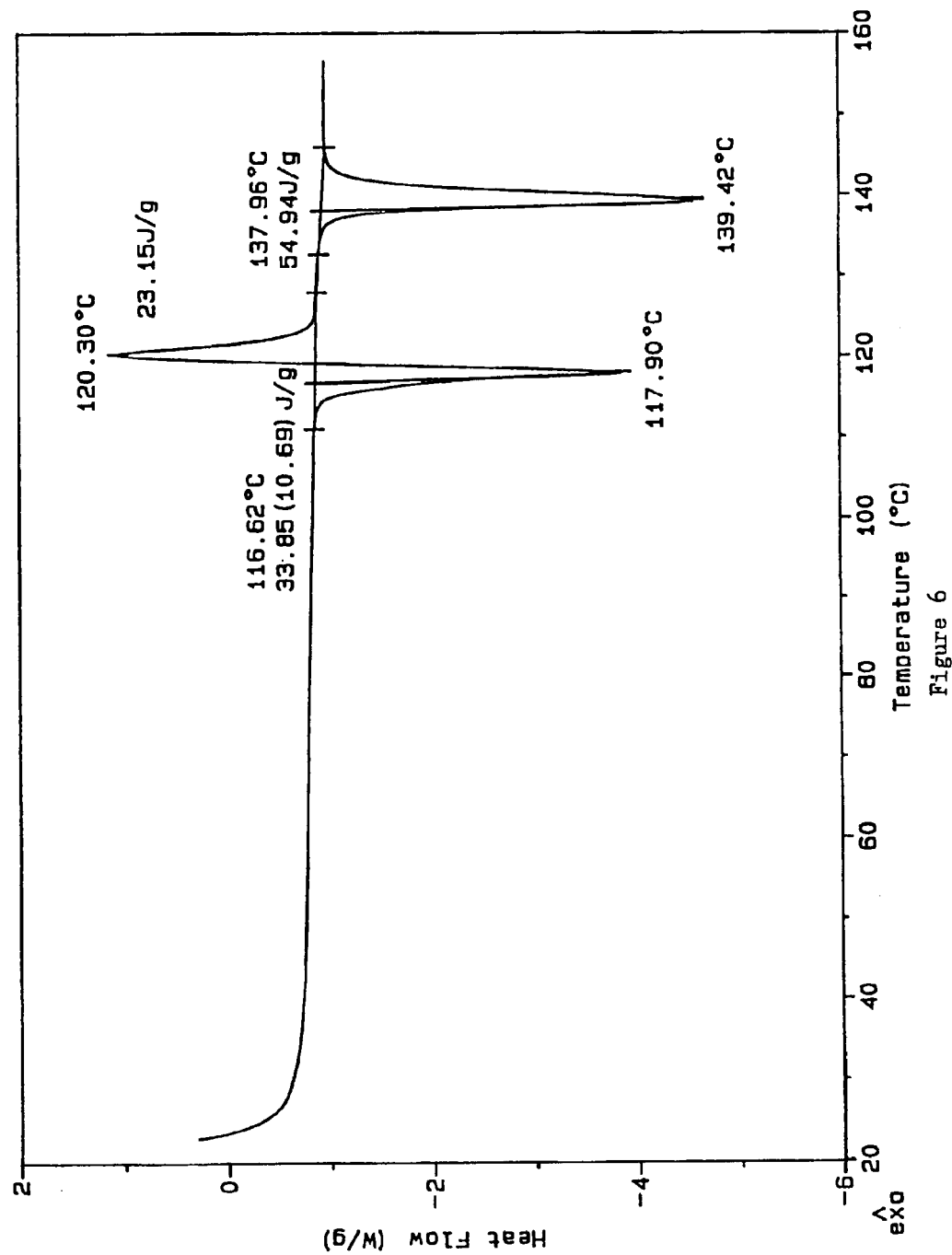
FIG. 6. DSC curve for Form III of (-)-6-chloro-4-cyclopropylethynyl-4-trifluoromethyl-1,4-dihydro-2H-3,1-benzoxazin-2-one.

FIGS. 3, 4 and 5 are the X-ray powder diffraction (XRPD) patterns for Forms I, II and III, respectively. These XRPD patterns were recorded using an automated X-ray diffractometer APD 3720 with copper K alpha radiation. The crystal forms I and II of (-)-6-chloro-4-cyclopropylethynyl-4-trifluoromethyl-1,4-dihydro-2H-3,1-benzoxazin-2-one which are characterized by the noted X-ray powder diffraction patterns have the following key diffraction peaks (2Θ) with intensities ($I/I_{max}$, %) of 10 or greater:

| Form I | Form II | Form III |
|--------|---------|----------|
| 6.0800 | 3.6375 | 7.2150 |
| 6.3900 | 6.3325 | 10.9675 |
| 10.3950 | 11.0725 | 13.7275 |
| 10.9875 | 12.7750 | 14.5325 |
| 12.2850 | 13.3275 | 16.7275 |
| 13.1900 | 14.2925 | 19.0675 |
| 14.1700 | 16.1200 | 19.6550 |
| 15.1925 | 16.8975 | 20.8250 |
| 16.9000 | 18.5025 | 21.7450 |
| 18.4375 | 19.1975 | 22.2825 |
| 19.2275 | 19.6025 | 22.8475 |
| 20.0925 | 20.6650 | 23.1750 |
| 21.2100 | 21.3250 | 23.8850 |
| 22.3600 | 22.6150 | 24.4900 |
| 23.0725 | 23.1775 | 24.9075 |
| 24.8900 | 24.4075 | 25.8200 |
| 25.9500 | 24.9650 | 27.0325 |
| 26.3575 | 26.0100 | 27.6050 |
| 27.2550 | 26.8550 | 29.2975 |
| 28.1150 | 27.6400 | 30.2600 |
| 28.5850 | 28.3675 | 30.7300 |
| 29.1325 | 29.1725 | 31.3125 |
| 29.5625 | 29.6325 | 33.3975 |
| 30.6850 | 30.5650 | 38.4325 |
| 32.3725 | 31.8950 | 39.2100 |
| 38.3125 | 33.8225 | |

Additionally, these crystal forms are characterized by peaks with varying D-spacings. Form I is characterized by peaks with D-spacings of: 14.5, 8.5, 8.0, 7.2, 6.7, 6.2, 5.2, 4.6, 4.4, 4.2, and 3.6 angstroms. Form II is characterized by peaks with D-spacings of: 24.3, 13.9, 8.0, 6.9, 6.6, 5.5, 4.6, 4.5, 4.3, 4.2, 3.9, 3.6, 3.4, 3.3, and 3.2 angstroms. Form III is characterized by peaks with D-spacings of: 12.2, 8.1, 6.4, 6.1, 4.7, 4.3, 4.1, 4.0, 3.9, 3.8, 3.7, 3.6, 3.3, 3.2, and 3.0 angstroms.

Figure 7:
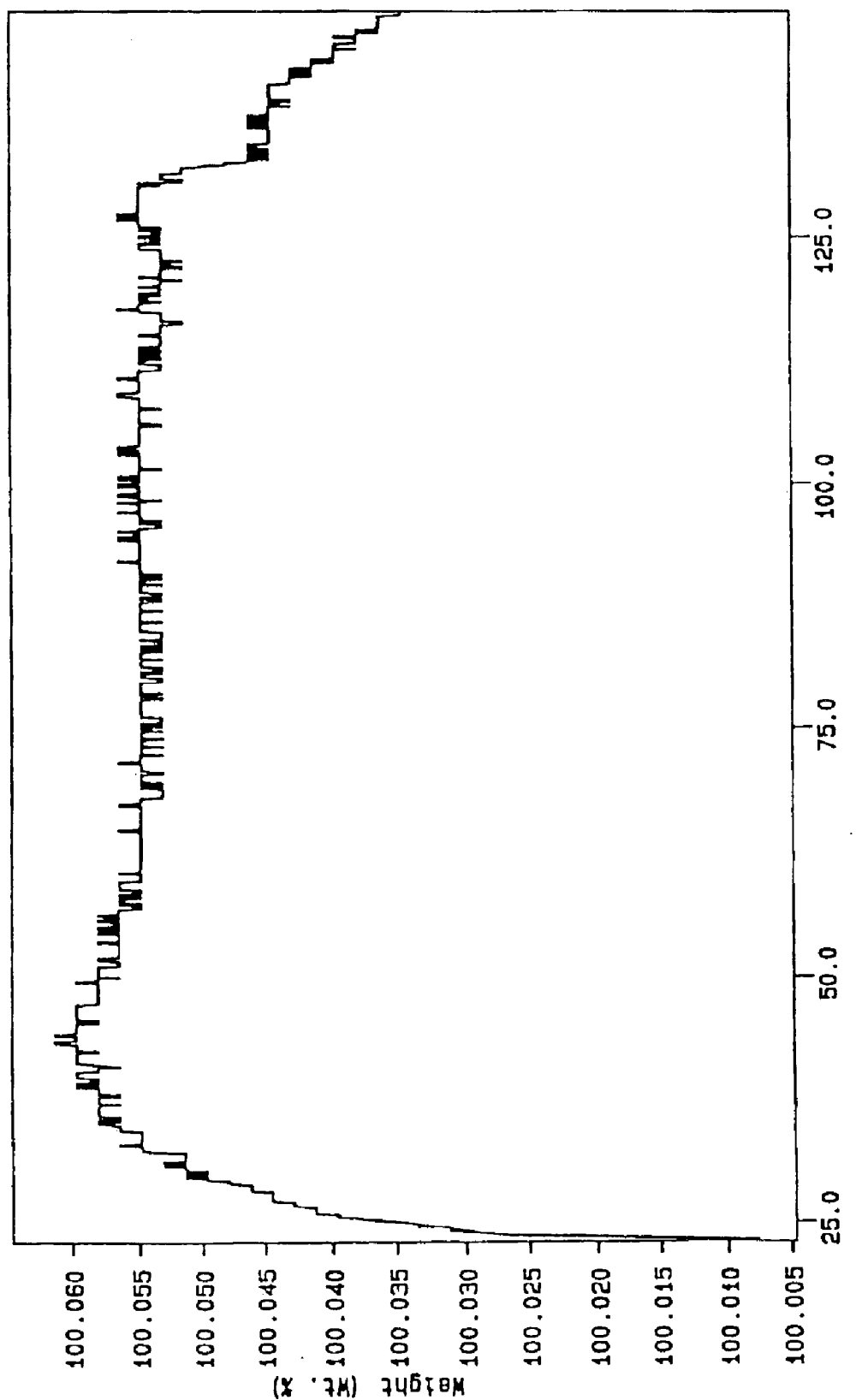
FIG. 7. TG analysis for Form III of (-)-6-chloro-4-cyclopropylethynyl-4-trifluoromethyl-1,4-dihydro-2H-3,1-benzoxazin-2-one.

Thermogravimetric analysis results of Form III (FIG. 7) indicated there was no significant weight loss observed from 43° C. to about 137° C. This result is indicative of an anhydrous or unsolvated crystal form.

The differential scanning calorimetry (DSC) results obtained for Form III show an endotherm with an extrapolated onset temperature of 117° C., a peak temperature of 118° C., and an enthalpy of 34 J/g, this is followed by an exotherm with a peak temperature of 120° C. and an enthalpy of 23 J/g. A second endotherm with an extrapolated onset temperature of 138° C., a peak temperature of 139° C., and an enthalpy of 55 J/g is also observed. The first endotherm is associated with the melting of Form III, which subsequently crystallizes to Form I during the exothermic event. The second endothermic event is associated with the melting of Form I.

A process for isolating (-)-6-chloro-4-cyclopropylethynyl-4-trifluoromethyl-1,4-dihydro-2H-3,1-benzoxazin-2-one, the final product from solutions containing an organic solvent and water has been developed. In this process water serves as an anti-solvent to produce a solid product from material dissolved in organic solvent. The final solvent composition is chosen to balance yield loss, purification, and slurry handling properties.

For methanol solvent systems about 40% to about 50% volume to volume (v/v) solvent to anti-solvent (water) has been present in the final slurry. Ethanol solvent systems have contained about 30% to about 40% v/v solvent to anti-solvent, and 2-propanol solvent systems have used about 25% to about 35% (v/v) solvent to anti-solvent. The total amount of liquid (alcohol and water) ranges from 12–20 ml/(g solid). The crystallizations are typically performed between 20–25° C., and some slurries have been cooled to 5–10° C. before being filtered. Following the filtration, the wetcake is washed with approximately one bed volume (the approximate volume of the wetcake) of the final crystallization solvent composition. The wetcake is then washed with at least 2 bed volumes of deionized (DI) water.

The rate at which the product is precipitated is controlled by either slowly adding the water to a saturated system following a seed charge (anti-solvent addition) or simultaneously adding the product in alcohol and water at controlled rates to an existing product slurry (heel crystallization).

For the anti-solvent process (FIG. 1), enough water is first added to the organic solvent solution containing the product over 0.5–2 hours to saturate the system in final product. A solid charge of final product is then added to the system as seed (2–10% of the initial amount of product). The seed should be Form I (the crystal form associated with dry final product) for ethanol and methanol systems, and Form II seed (the crystal form generated from a THF/heptane crystallization) is used for 2-propanol systems. The resultant slurry is aged for 0.5–2 hours to establish a seed bed. The remaining water is then added over 2–4 hours in a controlled manner. The slurry is then aged for 2–20 hours and cooled to the desired final temperature during the age, allowing the supernatant to reach equilibrium.

Figure 2:
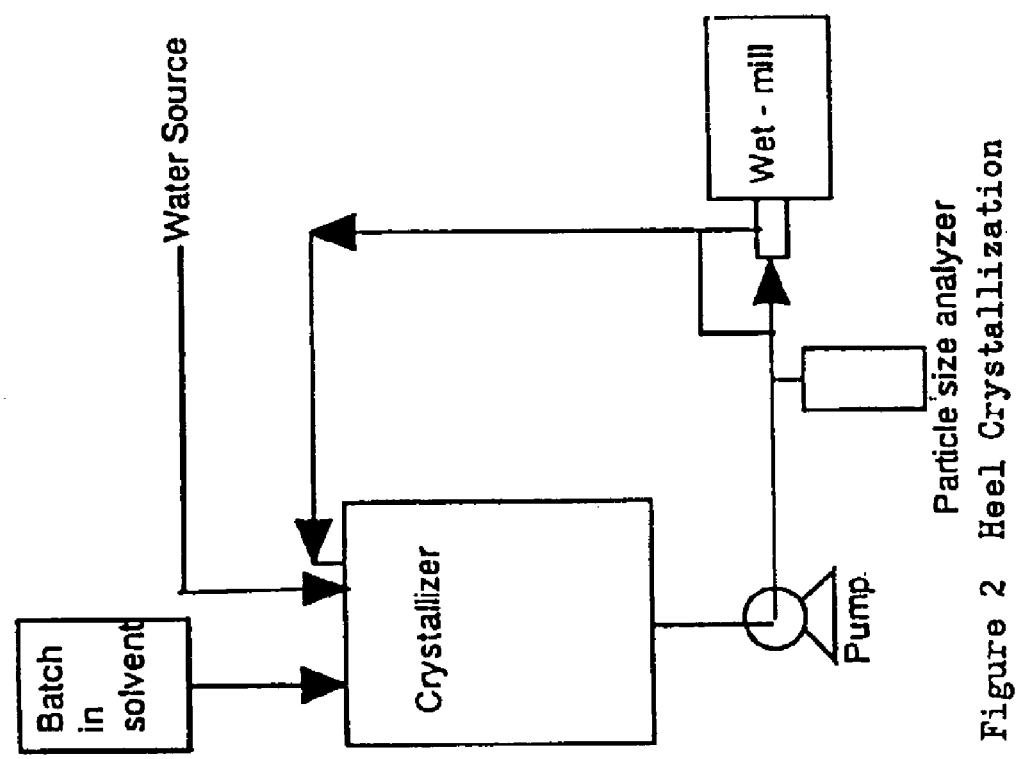
FIG. 2. Flowsheet of the heel crystallization method.

For the heel process (FIG. 2), a slurry at the desired final solvent composition is mixed while adding the product dissolved in alcohol and water at controlled relative rates to maintain a constant solvent ratio. The slurry (the crystalline compound in the final desired solvent system) is often 10–20% of the product from a prior run. The total charge is typically performed over 4–6 hours at 20–25° C. The slurry is then aged for several hours at the desired final temperature before being filtered to allow the supernatant to reach equilibrium. Following the filtration, the wetcake is washed with approximately one bed volume of a clean alcohol/water mixture matching the final crystallization conditions. The wetcake is then washed with at least 2 bed volumes of DI water.

Further control of the crystal size and slurry viscosity is achieved by using a wet-mill on slurries with excessively long particles and/or extremely thick consistencies. The product typically forms rod shaped crystals which grow much faster in the axial direction than the radial direction. It is understood that the reference to 'thickness' will refer to the crystal size and consistency of the slurry. The mill has been shown to reduce the length of the long crystals and produce a thin slurry from a thick slurry which contains many agglomerates of crystals. On the laboratory scale, the entire slurry can be milled batch-wise when desired. At larger scales, the wet-mill can be used on a recycle loop circulating around the crystallization vessel. An in-line particle size measurement and viscosity measurements could be coordinated to control the mill. Varying the temperature of the slurry through a range of 5° C. to 50° C. cycles has also been shown to be a useful way of modifying the crystal size and shape.

The solvents useful in this method include alcohol, acetonitrile (heel process only), dimethyl formamide (heel process only), and dimethyl acetamide (heel process only), The preferred solvent is an alcohol selected form methanol, ethanol or 2-propanol.

This crystallization process is advantageous over the prior method. The instant method allows one to isolate a crystalline product with consistent physical properties namely the ability to produce the desired crystal form of the product or convert to Form I with mild drying conditions (heating to about 40 to 60° C.). The alcohol-water crystallizations have also been shown to reject some impurities carried forward from the chemical synthesis. The final product slurry is less viscous and more homogenous with the instant process and is thus easier to mix and handle.

The following examples are meant to be illustrative of the present invention. These examples are presented to exemplify the invention and are not to be construed as limiting the scope of the invention.

EXAMPLE 1

Controlled Anti-Solvent Addition Crystallization Process 400 g of DMP-266 starting material is dissolved in 2.400 L of ethanol. See FIG. 1. The solution is filtered to remove extraneous matter. 2.088 L of deionized (DI) water is added to the solution over 30 to 60 minutes. 20 g of DMP-266 seed is added to the solution. The seed bed is aged for 1 hour. The use of Intermig agitators is preferred to mix the slurry. If required (by the presence of extremely long crystals or a thick slurry), the slurry is wet-milled for 15–60 seconds. 1.512 L of DI water is added to the slurry over 4 to 6 hours. If required (by the presence of extremely long crystals or a thick slurry), the slurry is wet-milled for 15 to about 60 seconds during the addition. The slurry is aged for 1 to 3 hours before being cooled to 10° C. over 3 hours. The slurry is aged for 2 to 16 hours until the product concentration in the supernatant remains constant. The slurry is filtered to isolate a crystalline wet cake. The wet cake is washed with 1 to 2 bed volumes of 40% ethanol in water and then twice with 2 L of DI water each. The washed wet cake is dried under vacuum at 50° C.

EXAMPLE 2

Semi-Continuous Heel Crystallization Process 400 g of DMP-266 starting material is dissolved in 2.400 L of ethanol. See FIG. 2. A heel slurry is produced by mixing 20 g of DMP-266 in 0.3 L of 40% (v/v) ethanol in water. The dissolved batch and 3.6 L of DI water are simultaneously charged to the heel slurry at constant rates over 6 hours to maintain a constant solvent composition in the crystallizer. Use of Intermig agitators during the crystallization is preferred. During this addition the slurry is wet-milled when the crystal lengths become excessively long or the slurry becomes too thick. The slurry is cooled to about 10° C. over 3 hours. The slurry is aged for 2 to 16 hours until the product concentration in the supernatant remains constant. The slurry is filtered to isolate a crystalline wet cake. The wet cake is washed with 1 to 2 bed volumes of 40% ethanol in water and then twice with 2 L of DI water each. The washed wet cake is dried under vacuum at 50° C.

EXAMPLES 3–8

Following the crystallization procedures described in Examples 1 and 2 above using the solvents noted in the table below in the amounts recited DMP-266 can be crystallized.

| Ex #: Solvent | ml solvent per g. DMP-266* | ml H$_2$O per g. DMP-266* | Anti-solvent Process | Heel Process |
|---|---|---|---|---|
| EX. 3: Acetonitrile | 3.6–8.0 | 7.2–14 | — | X |
| EX. 4: Dimethyl acetamide | 3.6–8.0 | 7.2–14 | — | X |
| EX. 5: Dimethyl formamide | 3.6–8.0 | 7.2–14 | — | X |
| EX. 6: Ethanol | 3.6–8.0 | 7.2–14 | X | X |
| EX. 7: Methanol | 4.8–10 | 5.4–12 | X | X |
| EX. 8: 2-Propanol | 3.0–7.0 | 7.8–15 | X | X |

*The sum of the amounts of solvent and water should be at least 12 ml/g. The currently preferred concentration is 15 ml/g.
— method did not work.
X method worked.

EXAMPLE 9

Crystallization of DMP-266 from 30% 2-Propanol in Water using a ratio of 15 ml solvent per gram DMP-266 Using Controlled Anti-Solvent Addition on a 400 g Scale 400 g. of DMP-266 starting material is dissolved in 1.8 L of 2-propanol. The solution is filtered to remove extraneous matter. 1.95 L of deionized (DI) water is added to the solution over 30 to 60 minutes. 10 g. to 20 g. of DMP-266 seed (Form II wetcake) is added to the solution. The seed bed is aged for 1 hour. The use of Intermig agitators is preferred to mix the slurry. If required (by the presence of extremely long crystals or a thick slurry), the slurry is wet-milled for 15–60 seconds. 2.25 L of DI water is added to the slurry over 4 to 6 hours. If required (by the presence of extremely long crystals or a thick slurry), the slurry is wet-milled for 15–60 seconds during the addition. The slurry is aged for 2 to 16 hours until the product concentration in the supernatant remains constant. The slurry is filtered to isolate a crystalline wet cake. The wet cake is washed with 1 to 2 bed volumes of 30% 2-propanol in water and then twice with 1 bed volume of DI water each. The washed wet cake is dried under vacuum at 50° C.

EXAMPLE 10

Crystallization of DMP-266 from 30% 2-Propanol in Water using a ratio of 15 ml solvent per gram DMP-266 Using a Semi-Continuous Process on a 400 g Scale 400 g. of DMP-266 starting material is dissolved in 1.8 L of 2-propanol. A heel slurry is produced by mixing 20 g. of Form II DMP-266 in 0.3 L of 30% (v/v) 2-propanol in water or retaining part of a slurry froma previous crystallization in the crystallizer. The dissolved batch and 4.2 L of DI water are simultaneously charged to the heel slurry at constant rates over 6 hours to maintain a constant solvent composition in the crystallizer. Use of Intermig agitators during the crystallization is preferred. During this addition the slurry is wet-milled when the crystal lengths become excessively long or the slurry becomes too thick. The slurry is aged for 2 to 16 hours until the product concentration in the supernatant remains constant. The slurry is filtered to isolate a crystalline wet cake. The wet cake is washed with 1 to 2 bed volumes of 30% 2-propanol in water and then twice with 1 bed volume of DI water each. The washed wet cake is dried under vacuum at 50° C.

What is claimed is:

1. Form I of (−)-6-chloro-4-cyclopropylethynyl-4-trifluoromethyl-1,4-dihydro-2H-3,1-benzoxazin-2-one, which is characterized by crystallographic D-spacings of 14.5, 8.5 and 7.2 Angstroms.

2. Form I according to claim 1, characterized by crystallographic D-spacings of 14.5, 8.5, 7.2, 6.2, 4.4 and 4.2 Angstroms.

3. Form I according to claim 2, characterized by crystallographic D-spacings of 14.5, 8.5, 8.0, 7.2, 6.7, 6.2, 4.4 and 4.2 Angstroms.

4. Form I according to claim 1, having no detectable peaks for Form II or Form III in its X-ray powder diffraction pattern.

5. Form II of (−)-6-chloro-4-cyclopropylethynyl-4-trifluoromethyl-1,4-dihydro-2H-3,1-benzoxazin-2-one, characterized by crystallographic D-spacings of 24.3, 6.9 and 5.5 Angstroms.

6. Form II according to claim 5, characterized by crystallographic D-spacings of 24.3, 13.9, 6.9, 6.6, 5.5 and 4.3 Angstroms.

7. Form II according to claim 6, characterized by crystallographic D-spacings of 24.3, 13.9, 8.0, 6.9, 6.6, 5.5, 4.5, 4.3, and 3.6 Angstroms.

8. Form II according to claim 5, having no detectable peaks for Form I or Form III in its X-ray powder diffraction pattern.

9. Form III of (−)-6-chloro-4-cyclopropylethynyl-4-trifluoromethyl-1,4-dihydro-2H-3,1-benzoxazin-2-one, characterized by crystallographic D-spacings of 12.2, 6.1 and 4.3 Angstroms.

10. Form III according to claim 9, characterized by crystallographic D-spacings of 12.2, 8.1, 6.1, 4.7, 4.3 and 4.1 Angstroms.

11. Form III according to claim 10, characterized by crystallographic D-spacings of 12.2, 8.1, 6.4, 6.1, 4.7, 4.3, 4.1, 3.7 and 3.6 Angstroms.

12. Form III according to claim 9, having no detectable peaks for Form I or Form II in its X-ray powder diffraction pattern.

13. Form III according to claim 9, which is further characterized by a DSC curve with a peak temperature of about 118° C. and an enthalpy of 34 J/g.

14. Form III according to claim 13, which is further characterized by a thermogravimetric analysis indicating no significant weight loss from 43° C. to 137° C.

* * * * *